United States Patent

Chang et al.

[11] Patent Number: 6,162,940
[45] Date of Patent: Dec. 19, 2000

[54] PROCESS FOR CO-PRODUCTION OF DIALKYL CARBONATE AND ALKANEDIOL

[75] Inventors: Clarence D. Chang, Princeton; Larry E. Hoglen, Mickleton; Zhaozhong Jiang, Thorofare; Rene B. LaPierre, Medford, all of N.J.

[73] Assignee: Mobil Oil Corporation, Fairfax, Va.

[21] Appl. No.: 09/460,757

[22] Filed: Dec. 14, 1999

[51] Int. Cl.$^7$ .................................................. C07C 68/06
[52] U.S. Cl. ........................................... 558/277; 568/858
[58] Field of Search .............................................. 558/277

[56] References Cited

U.S. PATENT DOCUMENTS

| | | |
|---|---|---|
| 3,642,858 | 2/1972 | Frevel et al. . |
| 4,062,884 | 12/1977 | Romano et al. . |
| 4,181,676 | 1/1980 | Buysch . |
| 4,391,739 | 7/1983 | Chu . |
| 4,434,105 | 2/1984 | Buysch et al. . |
| 4,661,609 | 4/1987 | Knifton . |
| 4,686,274 | 8/1987 | Harris et al. . |
| 4,691,041 | 9/1987 | Duranleau et al. . |
| 4,895,970 | 1/1990 | Harris . |
| 5,015,753 | 5/1991 | Harris . |
| 5,218,135 | 6/1993 | Buysch et al. . |
| 5,231,212 | 7/1993 | Buysch et al. . |
| 5,292,980 | 3/1994 | Dessau . |
| 5,387,708 | 2/1995 | Molzahn et al. . |
| 5,391,803 | 2/1995 | King et al. . |
| 5,430,170 | 7/1995 | Urano et al. . |
| 5,436,362 | 7/1995 | Kondoh et al. . |
| 5,489,703 | 2/1996 | Pacheco et al. . |
| 5,498,743 | 3/1996 | Shih et al. . |
| 5,663,480 | 9/1997 | Tsuneki et al. . |
| 5,847,189 | 12/1998 | Tojo et al. . |

FOREIGN PATENT DOCUMENTS

| | | |
|---|---|---|
| 0 478 073 A2 | 9/1991 | European Pat. Off. . |
| 3-44354 | 2/1991 | Japan . |
| 6-107601 | 4/1994 | Japan . |

OTHER PUBLICATIONS

Chang, C.D., *Handbook of Heterogenous Catalysis*, Wiley–VCH:Weinheim, Germany, vol. 4, Chapter 3.7 (1997).

Yagi, F., Kanuka, N., Tsuji, H., Nakata, S., Kita, H. and Hattori, H., "$^{133}$Cs and $^{23}$Na MAS NMR studies of zeolite X containing cesium," *Microporous Materials* 9:229–235(1997).

Skibsted, J., Vosegaard, T., Bildsøe, H. and Jakobsen, H.J., "$^{133}$Cs chemical Shielding Anisotropics and Quadrupole Couplings from Magic–Angle Spinning NMR of Cesium Salts," *J. Phys. Chem.*, 100:14872–14881(1996).

Knifton, J.F. and Duranleau, R.G., "Ethylene Glycol–Dimethyl Carbonate Cogeneration," *J. of Molecular Catalysis* 67:389–399(1991).

Watanabe, Y. and Tatsumi T., "Hydrotalcite–type Materials as Catalysts for the Synthesis of Dimethyl Carbonate from Ethylene Carbonate and Methanol[1]," *Microporous and Mesoporous Materials* 22:399–407(1998).

Primary Examiner—Michael G. Ambrose

[57] ABSTRACT

A method is provided for co-producing dialkyl carbonate and alkanediol by reacting alkylene carbonate with alkanol in the presence of a complex salt catalyst having a formula $A_x(M_yO_z)$, wherein A is an alkali metal or alkaline earth metal, M is a Group 5 or Group 6 transition metal, O is oxygen, x is 1 or 2, y is 1 or 2, and z is an integer from 3 to 6.

10 Claims, No Drawings

PROCESS FOR CO-PRODUCTION OF DIALKYL CARBONATE AND ALKANEDIOL

BACKGROUND

This invention relates to a method of co-producing dialkyl carbonate and alkanediol and, in particular, to a method of co-producing dialkyl carbonate and alkanediol through the use of a catalyst which is a complex salt compound.

Various homogeneous catalysts have been proposed for carbonate transesterification. For example, U.S. Pat. Nos. 3,642,858 and 4,181,676 disclose the preparation of dialkyl carbonates by transesterifying alkylene carbonates with alcohols in the presence of alkali metals or alkali metal compounds without the use of a support material. U.S. Pat. No. 4,661,609 teaches the use of a catalyst selected from the group consisting of zirconium, titanium and tin oxides, salts or complexes thereof.

Commercial use of homogeneous catalysts is restricted because separation of the catalyst from the unconverted reactants and organic product can be difficult. Because the transesterification is an equilibrium reaction, in an attempt to isolate the intended dialkyl carbonate by distillation of the reaction liquid without advance separation of the catalyst, the equilibrium is broken during the distillation and a reverse reaction is induced. Thus, the dialkyl carbonate once formed reverts to alkylene carbonate. Furthermore, due to the presence of the homogenous catalyst, side reactions such as decomposition, polymerization, or the like concurrently take place during the distillation which decrease the efficiency.

Various heterogenous catalysts have also been proposed for carbonate transesterification. The use of alkaline earth metal halides is disclosed in U.S. Pat. No. 5,498,743. Knifton, et al., "Ethylene Glycol-Dimethyl Carbonate Cogeneration," *J Molec. Catal.* 67:389–399 (1991) disclose the use of free organic phosphines or organic phosphines supported on partially cross-linked polystyrene. U.S. Pat. No. 4,691,041 discloses the use of organic ion exchange resins, alkali and alkaline earth silicates impregnated into silica, and certain ammonium exchanged zeolites. U.S. Pat. No. 5,430,170 discloses the use of a catalyst containing a rare earth metal oxide as the catalytically active component. The use of MgO is disclosed in Japanese Unexamined Patent Application 6[1994]-107,601. The use of $MgO/Al_2O_3$ hydrotalcites is disclosed in Japanese Unexamined Patent Application 3[1991]-44,354. Zeolites ion-exchanged with alkali metal and/or alkaline earth metal, thereby containing a stoichiometric amount of metal, are disclosed in U.S. Pat. No. 5,436,362.

European Patent Application 0 478 073 A2 discloses a process for producing a dialkyl carbonate by contacting an alkylene carbonate with an alkanol in the presence of a mixed metal oxide, i.e., a catalyst containing two or more metal oxides. Unlike the process disclosed in the European application, the method of the invention does not utilize a mixed metal oxide catalyst. Rather, the method of the invention utilizes a catalyst which is a single complex salt compound.

Inorganic heterogenous catalysts generally possess thermal stability and easy regeneration. However, these catalysts, including the zeolites containing a stoichiometric amount of alkali or alkaline earth metal, generally demonstrate low activity and/or selectivity and are unsatisfactory for commercial application. Polymer supported organic phosphines and ion exchange resins show high activity and good to excellent selectivity in transesterification reaction between alkylene carbonate and alkanol; however, these polymeric materials do not appear very stable and gradually lose catalytic activity, especially at relatively high temperatures.

Thus, there remains a need for a method of transesterifying alkylene carbonate with alkanol to co-produce dialkyl carbonate and alkanediol which will provide higher feed conversion and product selectivity over a wide temperature range.

SUMMARY OF INVENTION

A method is provided for co-producing dialkyl carbonate and alkanediol by reacting alkylene carbonate with alkanol in the presence of a complex salt catalyst having a formula $A_x(M_yO_z)$. A is a Group 1 alkali metal or Group 2 alkaline earth metal, M is a Group 5 or Group 6 transition metal, O is oxygen, x is 1 or 2, y is 1 or 2, and z is an integer from 3 to 6.

When M is a Group 5 transition metal and A is an alkali metal, a preferred formula for the catalyst is $A(MO_3)$ or $A_3(MO_4)$. When M is a Group 5 transition metal and A is an alkaline earth metal, a preferred formula for the catalyst is $A(M_2O_6)$.

When M is a Group 6 transition metal and A is an alkali metal, a preferred formula for the catalyst is $A_2(MO_4)$. Two preferred catalysts are $Na_2WO_4$ and $Na_2MoO_4$. When M is a Group 6 metal and A is an alkaline earth metal, a preferred formula for the catalyst is $A(MO_4)$.

Preferred alkali metals for the catalyst are potassium, sodium, cesium, or a combination thereof. Preferred Group 5 transition metals are vanadium, niobium, and tantalum. Preferred Group 6 metals are molybdenum and tungsten.

In a separate preferred embodiment, the catalyst is supported on an inorganic substrate. Preferred substrates are silica, alumina, zirconia, and mesopore materials, such as MCM-41 and MCM-48, or a combination of these substrates. Silica is most preferred.

The process conditions of the method of the invention include a reaction temperature of about 20° C. (68° F.) to about 300° C. (572° F.), a reaction pressure of about 14 to about 4000 psig, a liquid hourly space velocity of about 0.1 to 40 $hr^{-1}$, and a molar ratio of alkanol to alkylene carbonate of about 1–20.

Unlike polymer catalysts such as ion exchange resins, the complex salt catalysts used in the method of the invention are thermally stable and regenerable. The combination of high catalytic activity and selectivity in a wide temperature range, and excellent thermal stability and regenerability of the catalysts, render them suitable for commercial use in co-producing organic carbonate and alkanediol through ester exchange reaction. Also, the general availability and low cost of the catalysts could significantly improve the process economics.

The organic carbonates produced by the method of the invention, dimethyl carbonate in particular, have potential application as "green" replacements for phosgene that is used mainly in manufacture of polyurethane and polycarbonate resins.

DETAILED DESCRIPTION OF INVENTION

In accordance with the present invention, a method is provided for the co-production of dialkyl carbonate and alkanediol through the transesterification of alkylene carbonate with alkanol using a complex salt catalyst. The method includes reacting the alkylene carbonate with alkanol under process conditions in the presence of the complex salt catalyst.

The complex salt catalyst utilized in the method of the invention has the formula $A_x(M_yO_z)$ A is an alkali metal or alkaline earth metal, M is a Group 5 or Group 6 transition metal, O is oxygen, x is 1 or 2, y is 1 or 2, and z is an integer from 3 to 6.

The complex salt catalyst utilized in the process of the invention is a single compound which contains a polar anion. The anion is a complex anion because, unlike simple salts (e.g. NaCl), the transition metal of the catalyst is coordinated with oxygen anions.

The Group 5 metals are those listed as Group 5 (CAS version VB) of the Periodic Table of Elements. Preferred Group 5 metals include vanadium, niobium, and tantalum. The Group 6 metals are those listed as Group 6 (CAS version VIB) of the Periodic Table of Elements. Preferred Group 6 metals include molybdenum and tungsten.

Alkali metal is defined as those metals listed in Group 1 (IA) of the Periodic Table of Elements, or a combination thereof Alkaline earth metal is defined as those metals listed in Group 2 (IIA) of the Periodic Table of Elements, or a combination thereof. Preferred alkali metals include potassium, sodium, cesium, or a combination thereof While the mechanism is not completely understood, such alkali metals act as a weakly coordinating cation, creating a strong nucleophilic anionic coordinated complex, which may be associated with an increase in activity of the catalyst.

It is preferred that the stoichiometry of the catalyst compound be such that the catalyst is stable. For example, when A is an alkali metal and M is a Group 5 transition metal, preferred formulas for the complex salt catalyst are $A(MO_3)$ and $A_3(MO_4)$. Examples of such catalysts are $KVO_3$, $NaNbO_3$, $NaTaO_3$, and $Na_3VO_4$. When A is an alkaline earth metal and M is a Group 5 transition metal, a preferred formula is $A(M_2O_6)$. Examples of such catalysts are $MgV_2O_6$ and $MgNb_2O_6$ If A is an alkali metal and M is a Group 6 transition metal, a preferred formula for the catalyst is $A_2(MO_4)$. Examples of such catalysts are $Na_2WO_4$ and $Na_2MoO_4$, as demonstrated in the examples below. If A is an alkaline earth metal and M is a Group 6 transition metal, a preferred formula for the catalyst is $A(MO_4)$. Examples of such catalysts are $MgMoO_4$ and $CaWO_4$ (Scheelite).

The catalyst can be supported on a porous, inorganic substrate. Preferred porous inorganic substrates include silica, alumina, zirconia, mesoporous materials, such as MCM-41 and MCM-48, or a combination of these substrates. Silica is most prefered. The incorporation of the catalyst onto the substrate can be accomplished using any methods generally known, preferably by mixing the substrate with aqueous solution of the catalyst followed by evaporating/removing excess amount of water, drying the resultant supported catalyst at mild temperatures (50–150° C.), and calcining at high temperatures (>400° C.). During this procedure, the pH of the catalyst solution used is maintained at >7 to minimize possible formation of polyoxymetallate species.

In spite of the foregoing, polyoxymetallate species may still be present in the catalyst due to possible impurities in the commercial catalyst material and/or due to side reactions during the process for impregnation. If the polyoxymetallate species are present at all, it is preferred that they be present in an amount less than 10 wt %, more preferably less than 0.5 wt %. The presence of polyoxymetallate species in such amounts should only mildly affect the catalyst performance.

Generally, all alkylene carbonates can be used as a reactant in this invention. However, lower alkylene carbonate such as ethylene carbonate, propylene carbonate, butylene carbonate or the like is preferred; ethylene carbonate or propylene carbonate is most preferred.

Generally, all alkanol reactants can be used, provided the alkanol reacts with cyclocarbonate to produce the dialkyl carbonate and alkanediol product. However, an aliphatic or aromatic alkanol having 1 to 10 carbon atoms is preferably used. For example, methanol, ethanol, n-propanol, isopropanol, n-butanol, iso-butanol, secondary butanol, tertiary butanol, allyl alcohol, pentanol, cyclo-hexanol, benzyl alcohol, 2-phenyl ethyl alcohol, 3-phenyl propyl alcohol, 2-methoxy ethanol or the like can be used as the aliphatic or aromatic alcohol. A lower aliphatic alcohol such as methanol or ethanol is most preferably used due to its reactivity and low cost.

Further, a phenolic compound can be used in place of the alcoholic compound as the compound which has a hydroxyl (OH) group and reacts with cyclocarbonate to produce the carbonate.

The reactor type in this invention can be any type generally known such as a continuous fluid bed, fixed bed or stirred tank, etc. Since the catalyst used in the method of the invention is heterogenous, it is preferred that a fixed bed be used so as to avoid the expense of having to recover the catalyst from the reagents.

The reaction conditions of this invention include a reaction temperature of about 20° C. to about 300° C., preferably about 60° C. to about 175° C.; a reaction pressure of about 14 to about 4000 psig, preferably about 50 to about 400 psig; a liquid hourly space velocity of about 0.1 to about 40 $hr^{-1}$, preferably about 0.5 to about 10 $hr^{-1}$; and a molar ratio of alkanol to alkylene carbonate of about 1 to 20, preferably about 2 to 8.

The following comparative examples are provided to assist in a further understanding of the invention. The particular materials and conditions employed are intended to be further illustrative of the invention and are not limiting upon the reasonable scope thereof.

EXAMPLE 1

This example describes a method for preparing a catalyst employed in the method of the invention, i.e. silica supported $Na_2WO_4$ ($Na_2WO_4/SiO_2$).

Commercial sodium tungstate dihydrate (30.4 g) was dissolved in 500 cc de-ionized water, and the resultant solution was stirred and mixed with 200 g of silica gel (Davisil, grade 643, 200–425 mesh) for 2 h. At the end of this period, the mixture was evaporated to dryness at 60° C. using a rotary evaporator. The remaining solid catalyst was dried in an oven at 120° C. overnight and then calcined in air at 550° C. The calcined catalyst had a BET surface area of 116 $m^2/g$, and contained 1.9 wt % sodium and 6.6 wt % tungsten.

EXAMPLE 2

This example describes a method for preparing another catalyst employed in the method of the invention, i.e. silica supported $Na_2MoO_4$ ($Na_2MoO_4/SiO_2$).

Commercial sodium molybdate dihydrate (31.8 g) was dissolved in 500 cc de-ionized water, and the resultant solution was stirred and mixed with 200 g of silica gel (Davisil, grade 643, 200–425 mesh) for 2 h. At the end of this period, the mixture was evaporated to dryness at 60° C.

using a rotary evaporator. The remaining solid catalyst was dried in an oven at 120° C. overnight and then calcined in air at 550° C. The calcined catalyst had a BET surface area of 145 m²/g, and contained 2.6 wt % sodium and 5.8 wt % molybdenum.

EXAMPLE 3

Transesterification evaluations were performed using each of the catalysts described in Examples 1 and 2.

The transesterification reactions were performed in a fixed bed microunit equipped with a three-zone furnace and a down-flow trickle-bed tubular reactor (½" ID). Catalyst powder was pelletized and sized to 60–80 mesh. The reactor was loaded with a mixture of 10 cc of the sized catalyst and 3 cc of 80–120 mesh sand.

After pressure testing of the unit, the catalyst was dried at 400° F. for two hours under 1 atmosphere, 170 cc/min nitrogen flow. At the end of this period, the reactor was cooled down to 150° F. and nitrogen flow was stopped. The reactor pressure, controlled by a pressure regulator, was then set to 100 psi, and the EC/methanol mixture feed was pumped and added to the top of the reactor at 1.0 h$^{-1}$ LHSV. After the reactor was conditioned for 8 h, the reactor temperature was increased to initial operating temperature. Liquid products were condensed in a stainless steel dropout pot at −10° C. Both liquid and off-gas products were analyzed by GC. The catalytic reaction was studied at various temperatures and LHSV to vary EC conversion.

The two catalysts were evaluated according to the procedures described above. Detailed operating conditions and results on EC conversion and dimethyl carbonate (DMC)/ethylene glycol (EG) selectivities for $Na_2WO_4/SiO_2$ and $Na_2MoO_4/SiO_2$, are summarized in Tables 1 and 2, respectively.

Feed conversion is calculated based on EC converted during the transesterification reaction, since excess amount of methanol (relative to EC) was used for all reactions. During EC/MeOH reaction, 2-hydroxyethyl methyl carbonate (HEMC) intermediate was also formed in addition to DMC and EG. The concentration of HEMC varies depending on the reaction conditions.

Since it is recyclable along with unreacted EC, the intermediate carbonate is not considered as a byproduct. The feed conversion and product selectivity are defined as follows:

EC Conversion=(EC converted to products other than HEMC)/(total EC in feed)

DMC Selectivity=(moles of DMC formed)/(moles of EC converted to products other than HEMC)

EG Selectivity=(moles of EG formed)/(moles of EC converted to products other than HEMC).

TABLE 1

$Na_2WO_4/SiO_2$-Catalyzed Transesterification of Ethylene Carbonate with Methanol (Condition: 100 psig)

| Temperature, ° F./° C. | 300/149 | 325/163 | 350/177 | 300/149 | 325/163 |
|---|---|---|---|---|---|
| LHSV, h$^{-1}$ | 1.0 | 1.0 | 1.0 | 0.5 | 0.5 |
| Feed Composition | | | | | |
| MeOH/EC, molar ratio | 3.85 | 3.85 | 3.85 | 3.83 | 3.83 |
| Total Liquid Product Composition | | | | | |

TABLE 1-continued $Na_2WO_4/SiO_2$-Catalyzed Transesterification of Ethylene Carbonate with Methanol (Condition: 100 psig)

| Temperature, ° F./° C. | 300/149 | 325/163 | 350/177 | 300/149 | 325/163 |
|---|---|---|---|---|---|
| Composition | | | | | |
| MeOH, wt % | 45.7 | 47.1 | 48.5 | 45.1 | 46.9 |
| EC, wt % | 16.3 | 17.6 | 16.2 | 15.3 | 18.0 |
| HEMC Intermediate, wt %$^a$ | 11.2 | 8.9 | 11.3 | 8.3 | 8.0 |
| DMC, wt % | 15.0 | 15.4 | 13.8 | 18.2 | 15.9 |
| EG, wt % | 11.0 | 11.1 | 9.6 | 13.1 | 11.1 |
| DMC/EG, Molar Ratio | 0.94 | 0.96 | 0.99 | 0.96 | 0.99 |
| EC Conv., % | 38.9 | 39.3 | 36.4 | 46.6 | 39.9 |
| DMC Select., % | 94.3 | 96.3 | 96.2 | 95.6 | 98.1 |
| EG Select., % | 100.0 | 100.0 | 97.0 | 99.8 | 99.3 |

$^a$HEMC: 2-hydroxyethyl methyl carbonate - an intermediate carbonate formed during the reaction of ethylene carbonate with methanol

TABLE 2

$Na_2MoO_4/SiO_2$-Catalyzed Transesterification of Ethylene Carbonate with Methanol (Condition: 100 psig)

| Temperature, ° F./° C. | 300/149 | 325/163 |
|---|---|---|
| LHSV, h$^{-1}$ | 1.0 | 1.0 |
| Feed Composition | | |
| MeOH/EC, molar ratio | 3.95 | 3.95 |
| Total Liquid Product Composition | | |
| MeOH, wt % | 46.1 | 46.3 |
| EC, wt % | 16.8 | 19.1 |
| HEMC Intermediate, wt %$^a$ | 11.3 | 6.3 |
| DMC, wt % | 14.8 | 16.4 |
| EG, wt % | 11.0 | 11.7 |
| DMC/EG, Molar Ratio | 0.93 | 0.97 |
| EC Conv., % | 38.9 | 42.3 |
| DMC Select., % | 90.7 | 92.5 |
| EG Select., % | 97.7 | 95.6 |

$^a$HEMC: 2-hydroxyethyl methyl carbonate-an intermediate carbonate formed during the reaction of ethylene carbonate with methanol The examples demonstrate that the transesterification catalysts of the current invention exhibit good activity and very high selectivity in the reaction of alkylene carbonate with alkanol.

More specifically, $Na_2WO_4/SiO_2$ demonstrated an EC conversion of approximately 36–47% within the operating temperatures of 300 F–350° F. The conversion was lower at the higher operating temperature (350° F.) due to lower equilibrium constant with increasing temperature. The DMC selectivity was between approximately 94–98% for the full range of tested operating temperatures, i.e. 300 F–350° F. The EG selectivity was even greater at about 100% for the full range of operating temperatures.

Similarly, $Na_2MoWO_4/SiO_2$ demonstrated a good EC conversion i.e., approximately 39–42%, at a process temperature of 300–325° F. The DMC selectivity was between approximately 91–93%. The EG selectivity again was greater at about 96–98%.

Therefore, the method of the invention is adaptable to commercial application because of the good level of activity, very high selectivity over a wide temperature range, and the stability and relatively low cost of the transition metal compound catalyst used.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method for co-producing dialkyl carbonate and alkanediol comprising reacting alkylene carbonate with alkanol under process conditions in the presence of a complex salt catalyst having a formula $A_x(M_yO_z)$, wherein:

A is a Group 1 alkali metal or Group 2 alkaline earth metal,

M is a Group 5 or Group 6 transition metal,

O is oxygen, x is 1 or 2, y is 1 or 2, and z is an integer from 3 to 6.

2. A method as described in claim 1, wherein A is an alkali metal, wherein M is a Group 5 transition metal, and wherein said catalyst has a formula $A(MO_3)$ or $A_3(MO_4)$.

3. A method as described in claim 1, wherein A is an alkaline earth metal, wherein M is a Group 5 transition metal, and wherein said catalyst has a formula $A(M_2O_6)$.

4. A method as described in claim 1, wherein A is an alkali metal, wherein M is a Group 6 metal, and wherein said catalyst has a formula $A_2(MO_4)$.

5. A method as described in claim 1, wherein A is an alkaline earth metal, wherein M is a Group 6 metal, and wherein said catalyst has a formula $A(MO_4)$.

6. A method as described in claim 1 wherein said catalyst is $Na_2WO_4$ or $Na_2MoO_4$.

7. A method as described in claim 1, wherein said alkali metal is selected from the group consisting of potassium, sodium, cesium, or a combination thereof; wherein said Group 5 metal is selected from the group consisting of vanadium, niobium, and tantalum; and wherein said Group 6 metal is selected from the group consisting of molybdenum and tungsten.

8. A method as described in claim 1 wherein said catalyst is supported on a porous inorganic substrate.

9. A method as described in claim 8 wherein said substrate is selected from the group consisting of silica, alumina, zirconia, mesoporous materials, or a combination thereof.

10. The method of claim 1 wherein said process conditions comprise a reaction temperature of about 20° C. to about 300° C., a reaction pressure of about 14 to about 4000 psig, a liquid hourly space velocity of about 0.1 to about 40 $hr^{-1}$, and a molar ratio of alkanol to alkylene carbonate of about 1–20.

* * * * *

UNITED STATES PATENT AND TRADEMARK OFFICE
CERTIFICATE OF CORRECTION

PATENT NO.   : 6,162,940
DATED        : December 19, 2000
INVENTOR(S)  : Clarence D. Change et al.

It is certified that error appears in the above-identified patent and that said Letters Patent is hereby corrected as shown below:

<u>Title page,</u>
Item [57], ABSTRACT,
Line 6, delete "x is 1 or 2" and insert therefor -- x is 1, 2 or 3 --.

<u>Column 2,</u>
Line 18, delete "x is 1 or 2" and insert therefor -- x is 1, 2 or 3 --.

<u>Column 3,</u>
Line 6, delete "x is 1 or 2" and insert therefor -- x is 1, 2 or 3 --.

<u>Column 7,</u>
Line 15, delete "x is 1 or 2" and insert therefor -- x is 1, 2 or 3 --.

Signed and Sealed this

Thirtieth Day of December, 2003

JAMES E. ROGAN
*Director of the United States Patent and Trademark Office*